US012100139B2

(12) United States Patent
Miyamoto et al.

(10) Patent No.: US 12,100,139 B2
(45) Date of Patent: Sep. 24, 2024

(54) IMAGE PROCESSING APPARATUS, IMAGE PROCESSING METHOD, AND COMPUTER-READABLE STORAGE MEDIUM FOR DETERMINING A RADIATION FIELD OF RADIATION FROM A RADIATION IMAGE

(71) Applicant: CANON KABUSHIKI KAISHA, Tokyo (JP)

(72) Inventors: Hideaki Miyamoto, Tokyo (JP); Haruki Iwai, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 588 days.

(21) Appl. No.: 17/350,000

(22) Filed: Jun. 17, 2021

(65) Prior Publication Data

US 2021/0407079 A1     Dec. 30, 2021

(30) Foreign Application Priority Data

Jun. 25, 2020   (JP) ................................. 2020-109951

(51) Int. Cl.
   *G06T 7/00*     (2017.01)
   *G06T 7/70*     (2017.01)

(52) U.S. Cl.
   CPC .............. *G06T 7/0012* (2013.01); *G06T 7/70* (2017.01); *G06T 2207/10121* (2013.01); *G06T 2207/20104* (2013.01)

(58) Field of Classification Search
   CPC .................... G06T 7/0012; G06T 7/70; G06T 2207/10121; G06T 2207/20104
   (Continued)

(56) References Cited

U.S. PATENT DOCUMENTS

2001/0046312 A1    11/2001   Murakami
2019/0356846 A1*   11/2019   Nishii ................... H04N 23/80
(Continued)

FOREIGN PATENT DOCUMENTS

| EP | 2241254 A1   | 10/2010 |
|----|--------------|---------|
| JP | H07-87397 A  | 3/1995  |

(Continued)

OTHER PUBLICATIONS

Extended European Search Report issued by the European Patent Office on Nov. 30, 2021 in corresponding EP Patent Application No. 21180871.2.

(Continued)

*Primary Examiner* — Gabriel I Garcia
(74) *Attorney, Agent, or Firm* — Carter, DeLuca & Farrell LLP

(57) ABSTRACT

An image processing apparatus for determining a radiation field of radiation from a radiation image comprises: a prediction unit that predicts, based on prior information, a degree that each position of the radiation image becomes a predetermined portion of the radiation field and generating a prediction result representing a distribution of the predicted degrees; an analysis unit that analyzes the radiation image to determines the degree that each position of the radiation image becomes the predetermined portion of the radiation field and generating an analysis result representing the distribution of the predicted degrees; and a recognition unit that decides the predetermined portion of the radiation field based on a combining result obtained by combining the prediction result and the analysis result.

20 Claims, 8 Drawing Sheets

(58) Field of Classification Search
USPC .......................................................... 382/132
See application file for complete search history.

(56) References Cited

U.S. PATENT DOCUMENTS

| | | |
|---|---|---|
| 2020/0057907 A1 | 2/2020 | Kobayashi |
| 2021/0158105 A1 | 5/2021 | Machida et al. |
| 2021/0158218 A1 | 5/2021 | Machida et al. |

FOREIGN PATENT DOCUMENTS

| | | |
|---|---|---|
| JP | 2010-246778 A | 11/2010 |
| JP | 2013-128585 A | 7/2013 |
| JP | 2020-25780 A | 2/2020 |
| WO | 2010/147075 A1 | 12/2010 |

OTHER PUBLICATIONS

Notice of Reasons for Refusal issued by the Japanese Patent Office on Oct. 27, 2023 in corresponding JP Patent Application No. 2020-109951, with English translation.

\* cited by examiner

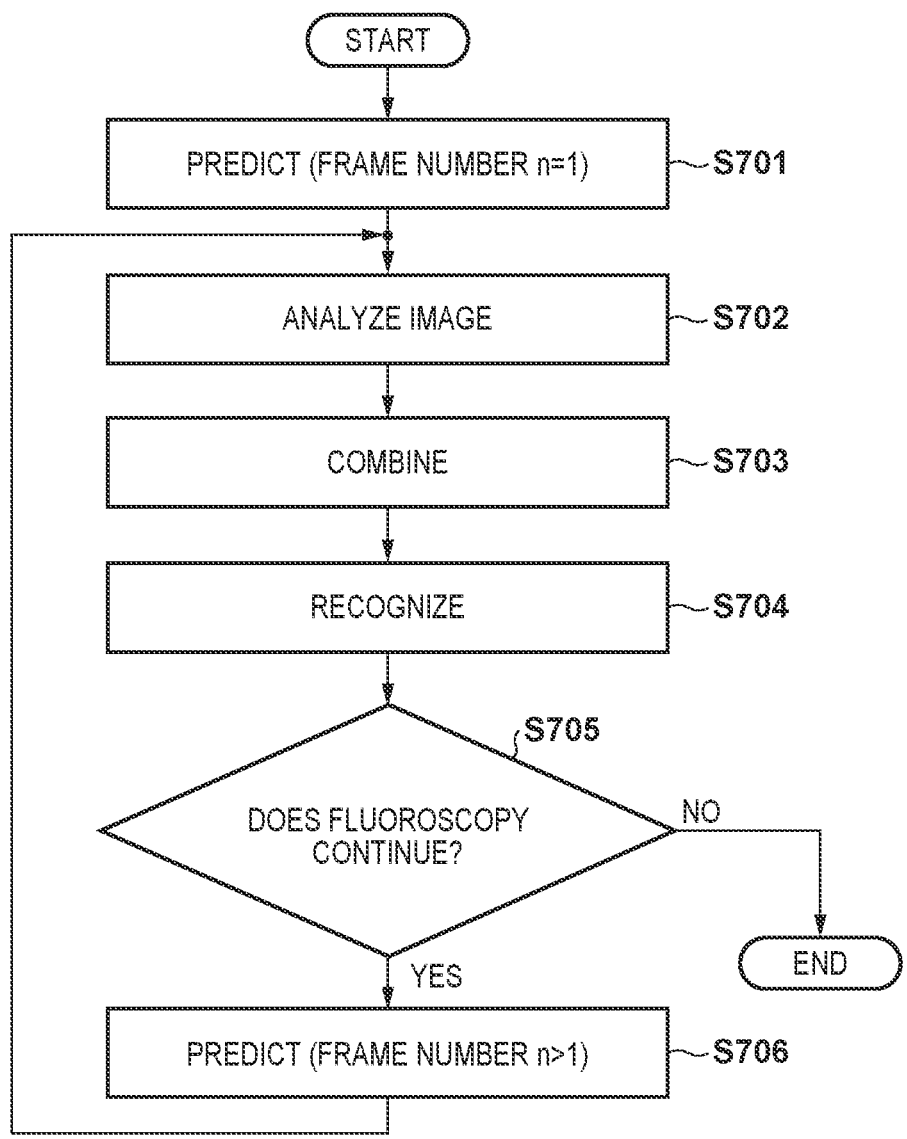

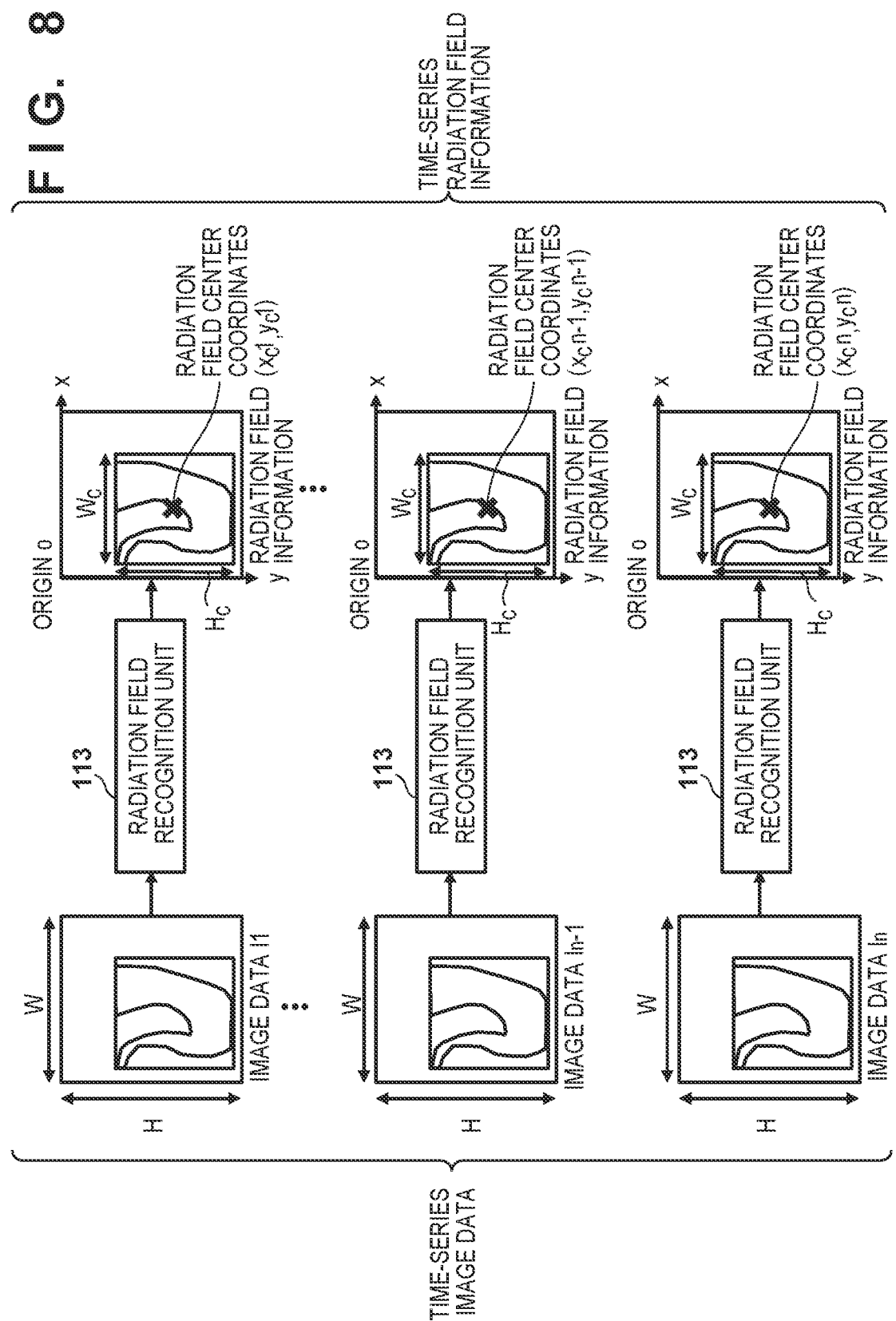

IMAGE PROCESSING APPARATUS, IMAGE PROCESSING METHOD, AND COMPUTER-READABLE STORAGE MEDIUM FOR DETERMINING A RADIATION FIELD OF RADIATION FROM A RADIATION IMAGE

BACKGROUND OF THE INVENTION

Field of the Invention

The present invention relates to an image processing apparatus that acquires a medical image by fluoroscopy and imaging using, for example, radiation, an image processing method, and a computer-readable storage medium.

Description of the Related Art

In the medical filed, radiation imaging apparatuses that obtain a fluoroscopic image of an object by irradiating an object with radiation and detecting the radiation transmitted through the object are widely used. In a radiation imaging apparatus of this type, a radiation diaphragm is provided in a radiation irradiation unit, and partial fluoroscopic imaging using only a range necessary for diagnosis as a radiation field is performed using the radiation diaphragm (for example, Japanese Patent Laid-Open No. 2013-128585). Such partial fluoroscopic imaging is very useful because it can suppress unnecessary radiation irradiation for an object that is a human body and reduce the radiation exposure dose of the object.

Since the radiation field is limited, a captured image obtained by partial fluoroscopic imaging includes not only a radiation field region having information useful for diagnosis but also a region outside the radiation field, which has no information useful for diagnosis. The region outside the radiation field is a region unnecessary for diagnosis. Hence, for example, when displaying an image captured by partial fluoroscopic imaging on a display apparatus, it is effective to mask only the region outside the radiation field, cut out the radiation field region and display it in a large size, or set the region outside the radiation field outside the range of feature amount calculation processing for tone processing.

To perform the processing as described above, a radiation imaging apparatus is required to include a radiation field recognition device configured to discriminate an irradiation region on an image and a region outside a radiation field. Particularly in radioscopy in which a place appropriate as a radiation field is searched for by moving a radiation diaphragm while generating a radiation image at 15 to 30 frames/sec, radiation field recognition is required to have real time property and stability for suppressing a failure or a vibration.

SUMMARY OF THE INVENTION

The present invention provides a technique of performing radiation field recognition with real time property and stability.

According to one aspect of the present invention, there is provided an image processing apparatus for determining a radiation field of radiation from a radiation image, comprising: a prediction unit configured to predict, based on prior information, a degree that each position of the radiation image becomes a predetermined portion of the radiation field and generate a prediction result representing a distribution of the predicted degrees; an analysis unit configured to analyze the radiation image to determines the degree that each position of the radiation image becomes the predetermined portion of the radiation field and generate an analysis result representing the distribution of the predicted degrees; and a decision unit configured to decide the predetermined portion of the radiation field based on a combining result obtained by combining the prediction result and the analysis result.

According to another aspect of the present invention, there is provided an image processing method of determining a radiation field of radiation from a radiation image, comprising: predicting, based on prior information, a degree that each position of the radiation image becomes a predetermined portion of the radiation field and generating a prediction result representing a distribution of the predicted degree; analyzing the radiation image to determines the degree that each position of the radiation image becomes the predetermined portion of the radiation field and generating an analysis result representing the distribution of the predicted degree; and deciding the predetermined portion of the radiation field based on a combining result obtained by combining the prediction result and the analysis result.

According to another aspect of the present invention, there is provided a non-transitory computer-readable storage medium storing a program for causing a computer to execute an image processing method of determining a radiation field of radiation from a radiation image, the method comprising: predicting, based on prior information, a degree that each position of the radiation image becomes a predetermined portion of the radiation field and generating a prediction result representing a distribution of the predicted degree; analyzing the radiation image to determines the degree that each position of the radiation image becomes the predetermined portion of the radiation field and generating an analysis result representing the distribution of the predicted degree; and deciding the predetermined portion of the radiation field based on a combining result obtained by combining the prediction result and the analysis result.

According to another aspect of the present invention, there is provided an image processing apparatus for deciding a radiation field region of a time-serially acquired radioscopic image, comprising: a prediction unit configured to predict a predetermined portion of a radiation field in a target fluoroscopic image that is a radioscopic image of a decision target based on prior information acquired before the target fluoroscopic image and acquiring prediction information representing a prediction result of the prediction; an analysis unit configured to analyze the target fluoroscopic image and acquiring image information representing the predetermined portion of the radiation field in the target fluoroscopic image; and a decision unit configured to decide the radiation field region of the target fluoroscopic image based on the prediction information and the image information.

Further features of the present invention will become apparent from the following description of exemplary embodiments with reference to the attached drawings.

BRIEF DESCRIPTION OF THE DRAWINGS

FIG. 7 is a flowchart showing the processing procedure of a radiation field recognition unit 113 according to the second embodiment; and FIG. 8 is a view showing an example of an input/output of the radiation field recognition unit 113 according to the second embodiment.

DESCRIPTION OF THE EMBODIMENTS

Figure 1:
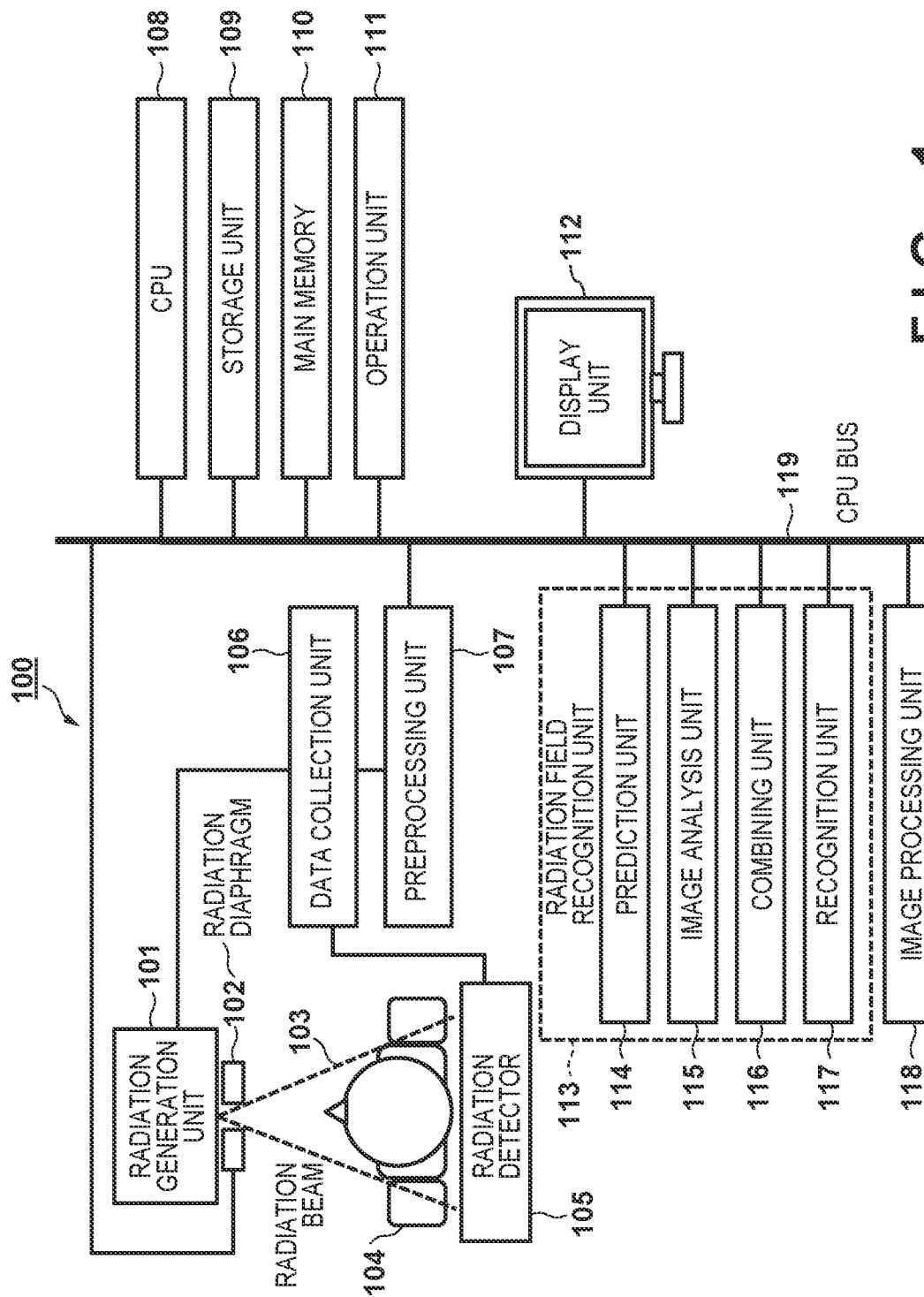
FIG. 1 is a view showing an example of the schematic configuration of a radiation imaging apparatus according to the first embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate.

Furthermore, in the attached drawings, the same reference numerals are given to the same or similar configurations, and redundant description thereof is omitted.

First Embodiment (Schematic Configuration)

FIG. 1 is a view showing an example of the configuration of a radiation imaging apparatus 100 according to the first embodiment. The radiation imaging apparatus 100 includes a radiation generation unit 101, a radiation diaphragm 102, a radiation detector 105, a data collection unit 106, a preprocessing unit 107, a CPU 108, a storage unit 109, a main memory 110, an operation unit 111, a display unit 112, a radiation field recognition unit 113, and an image processing unit 118. The units are connected via a CPU bus 119 and can transmit/receive data to/from each other.

The main memory 110 stores various kinds of programs to be executed by the CPU 108, and also functions as a working memory necessary for processing of the CPU 108. The CPU 108 executes a predetermined program stored in the main memory 110, thereby performing operation control of the entire apparatus in accordance with a user operation from the operation unit 111 and parameters stored in the storage unit 109.

When an imaging instruction is input from the user via the operation unit 111, the imaging instruction is transmitted to the data collection unit 106 by the CPU 108. Upon receiving the imaging instruction, the data collection unit 106 controls the radiation generation unit 101 and the radiation detector 105 and causes these to execute radiation imaging. In the radiation imaging, first, the radiation generation unit 101 irradiates an object 104 with a radiation beam 103. The object 104 is a target of radiation imaging. The radiation beam 103 emitted by the radiation generation unit 101, whose irradiation range is limited by the radiation diaphragm 102, passes through the object 104 and reaches the radiation detector 105. The radiation detector 105 outputs a signal according to the intensity of the radiation beam 103 that has reached. The radiation diaphragm 102 is formed by, for example, diaphragm blades made of plates of lead or the like and arranged on the upper, lower, left, and right sides, respectively, and forms a rectangular opening. The radiation diaphragm 102 is configured such that, for example, the diaphragm blades on the upper, lower, left, and right sides can asymmetrically move based on radiation diaphragm control information supplied from the CPU 108. Hence, the radiation field of radiation with which the radiation detector 105 is irradiated is set to an arbitrary position. The data collection unit 106 converts the signal output for the radiation detector 105 into a digital signal and supplies it as image data to the preprocessing unit 107. The preprocessing unit 107 performs preprocessing such as offset correction and gain correction for the image data supplied from the data collection unit 106. The image data that has undergone the preprocessing by the preprocessing unit 107 is transferred to the main memory 110, the radiation field recognition unit 113, and the image processing unit 118 via the CPU bus 119.

The main memory 110 stores the transferred image data. The radiation field recognition unit 113 recognizes, from the transferred image data, the radiation field of the radiation with which the radiation detector 105 is irradiated, and outputs radiation field information representing the recognized radiation field. The radiation field corresponds to a region of the radiation detector 105 irradiated with the radiation. The image processing unit 118 performs image processing based on the radiation field information output from the radiation field recognition unit 113 for the transferred image data. The image processing can include, for example, tone processing based on the statistic values (the average value, the maximum/minimum value, and the like) of pixel values belonging to the radiation field, cut-out/enlargement processing of pixels belonging to the radiation field, and mask processing of pixels that do not belong to the radiation field. The radiation field information and the image data that has undergone image processing are transferred to, for example, the storage unit 109 and the display unit 112 via the CPU bus 119 as image data that has undergone image processing. The storage unit 109 stores the transferred radiation field information and the image data that has undergone image processing. The display unit 112 displays the transferred radiation field information and the image data that has undergone image processing. A user can confirm the radiation field information and the image data that has undergone image processing, which are displayed on the display unit 112, and input an operation instruction via the operation unit 111 as needed.

(Radiation Field Recognition Procedure)

Figure 2:
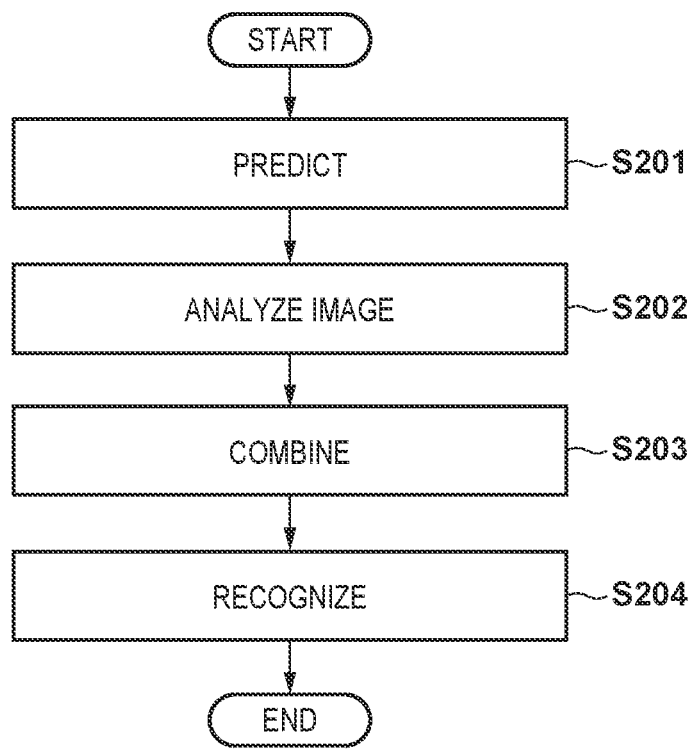
FIG. 2 is a flowchart showing the processing procedure of a radiation field recognition unit 113 according to the first embodiment.
Figure 3:
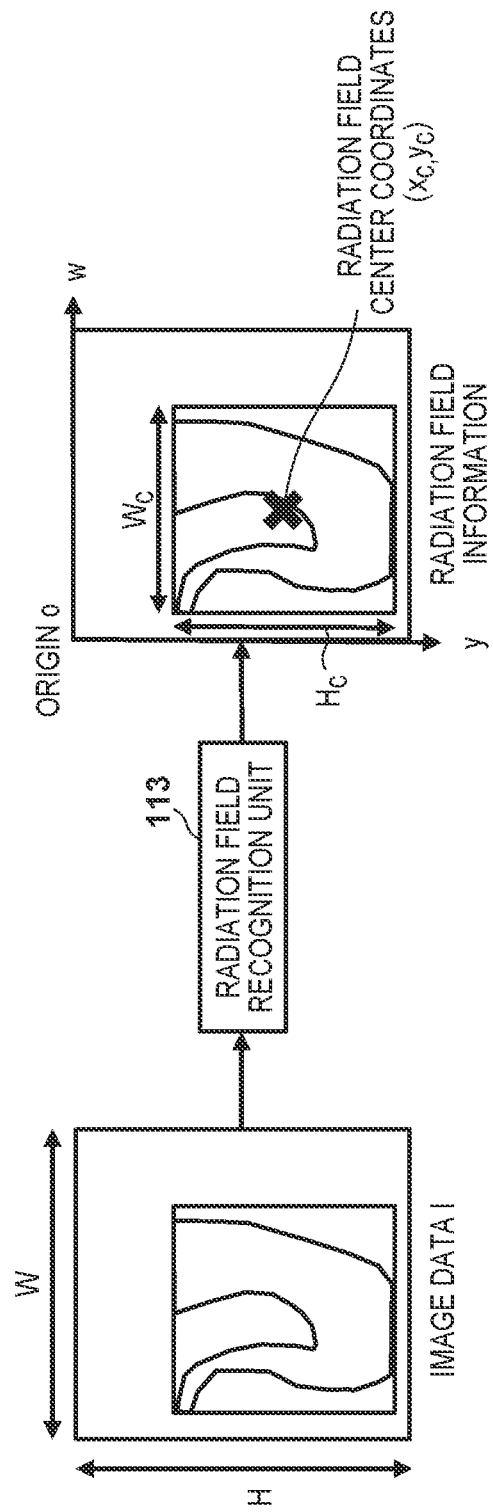
FIG. 3 is a view showing an example of an input/output of the radiation field recognition unit 113 according to the first embodiment.

The radiation field recognition unit 113 includes a prediction unit 114, an image analysis unit 115, a combining unit 116, and a recognition unit 117. An operation of the radiation field recognition unit 113 to recognize a radiation field from a radiation image (image data) and output radiation field information will be described below in detail with reference to a flowchart shown in FIG. 2. Note that radiation field information is not particularly limited, and in this embodiment, a case in which center coordinates ($x_c$, $y_c$) of a radiation field having a rectangular shape in a fixed size ($W_c$, $H_c$) are obtained as radiation field information from image data I having a size (W, H) will be described as an example (FIG. 3). Note that the shape of the radiation field is not limited to a rectangular shape and may be another polygonal shape. In addition, a coordinate in this embodiment is an index on an image when the upper left corner of the image data I is defined as an origin O.

[Step S201]

Figure 4:
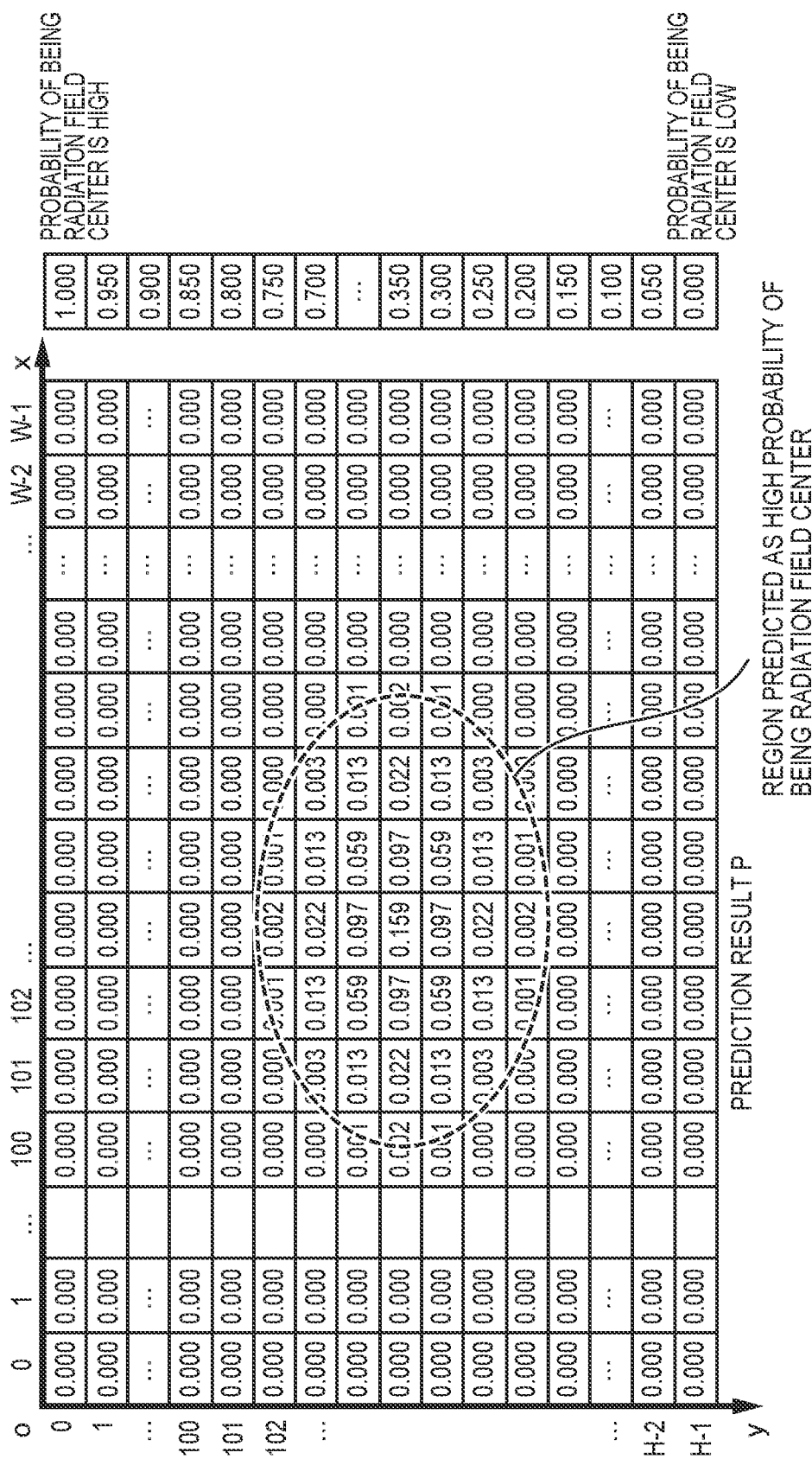
FIG. 4 is a view showing an example of an output of a prediction unit 114.

The prediction unit 114 predicts a radiation field for a transferred radiation image (image data I) based on prior information (to be described later) and generates a prediction result P. The prediction unit 114 predicts, based on the prior information, the degree that each position (for example, each pixel) of the image data I becomes a predetermined portion of the radiation field, and generates the prediction result P representing the distribution of predicted degrees. In this example, the predetermined portion of the radiation field is a radiation field center. The prediction result P is obtained as, for example, image data having, as a pixel value, a value representing a probability that a pixel value is a radiation field center. In this embodiment, for example, as shown in FIG. 4, the prediction result P is image data having the same size (W, H) as the image data I, and the probability that a value P(x, y) at coordinates (x, y) is a radiation field center is represented by a value from 0 to 1. However, the form of the prediction result P is not limited to this. Also, concerning a method of generating the prediction result P by the prediction unit 114, several examples will be described below. However, the method is not limited to these.

(Prediction Result Generation Method 1)

The prediction unit 114 loads prior information included in parameters stored in the storage unit 109, and generates the prediction result P based on the prior information. Here, the prior information is information representing that, for example, the distribution of radiation field centers in radiation imaging using the radiation imaging apparatus 100 complies with (or can be approximated to) a predetermined distribution function with respect to coordinates $(x_i, y_i)$ as the center. Here, as the predetermined distribution function, for example, a normal distribution of standard deviations σ can be applied. At this time, the prediction unit 114 generates the prediction result P by $$P(x, y) = \frac{1}{2\pi\sigma^2} \exp\left\{-\frac{(x-x_i)^2 + (y-y_i)^2}{2\sigma^2}\right\} \quad (1)$$

The range of (x, y) in equation (1) becomes larger than 0. If the value P(x, y) is sufficiently small at the coordinates (x, y) that cannot be a radiation field center, the prediction unit 114 sets the value P(x, y) to 0. Accordingly, coordinates whose probability of being a radiation field is 0 are set. In addition, $\sigma^2 \leq \pi/2$ is set such that the value P(x, y) becomes 1 or less. Here, σ is a parameter for controlling the spread of a probability distribution representing the prediction result P. For example, σ is set to a large value if the reliability of a radiation field center by prediction is low, and set to a small value if the reliability is high. Hence, the maximum value of P(x, y) takes a value smaller than 1. Note that the prior information may include the set value of σ. The prior information may also include information for designating the distribution function used to generate the prediction result P.

(Prediction Result Generation Method 2)

If a plurality of coordinate points $(x_i, y_i)$ as radiation field centers exist in prior information, the prediction result P may be obtained using equation (1) for each of the plurality of coordinate points, and a plurality of obtained prediction results P may be combined. For example, assume that prior information represents three radiation field centers, and indicates that prediction results are combined by multiplication. In this case, the prediction unit 114 acquires, for example, three prediction results $P_1$, $P_2$, and $P_3$ concerning the three radiation field centers using equation (1), and combines there using equation (2), thereby generating the prediction result P.

$$P(x,y)=P_1(x,y)P_2(x,y)P_3(x,y) \quad (2)$$

(Prediction Result Generation Method 3)

Also, the prediction unit 114 may set a radiation field center $(x_i, y_i)$ using, for example, information concerning an object that is the target of radiation imaging as prior information. For example, if a radiation field center is defined based on information such as the physical size, the imaging part, or the like of an object, the prediction unit 114 sets the radiation field center $(x_i, y_i)$ using, as prior information, any one of these pieces of information input by the user in advance via the operation unit 111, and generates the prediction result P. Alternatively, if the user directly inputs the designation of the radiation field center from the operation unit 111, the prediction unit 114 may generate the prediction result P using the designated radiation field center as prior information. If the radiation field center can directly be input, the deviation between the input radiation field center and the actual radiation field center is derived only from, for example, physical arrangement errors and the like of the radiation generation unit 101, the radiation diaphragm 102, and the radiation detector 105, and the reliability of prior information becomes high. If the reliability of the prior information is high, for example, if the prediction result P is obtained by equation (1), a more appropriate prediction result P considering the reliability of the prior information can be generated by making the standard deviation σ in equation (1) small.

(Prediction Result Generation Method 4)

Alternatively, a radiation field recognition result of image data $I_{prev}$ captured in the past may be used as prior information. In this case, the radiation field recognition unit 113 stores, in the storage unit 109, the radiation field recognition result of the past image data $I_{prev}$ or a calculation result obtained halfway through radiation field recognition. The prediction unit 114 reads out these from the storage unit 109 as prior information. For example, the radiation field recognition unit 113 stores, in the storage unit 109, a combining result $C_{prev}$ obtained by combining a prediction result and an analysis result for the past image data $I_{prev}$. The prediction unit 114 reads out the combining result $C_{prev}$ from the storage unit 109 and obtains as the prediction result P of the image data I. The combining result $C_{prev}$ will be described later.

$$P(x,y)=C_{prev}(x,y) \quad (3)$$

[Step S202]

Figure 5:
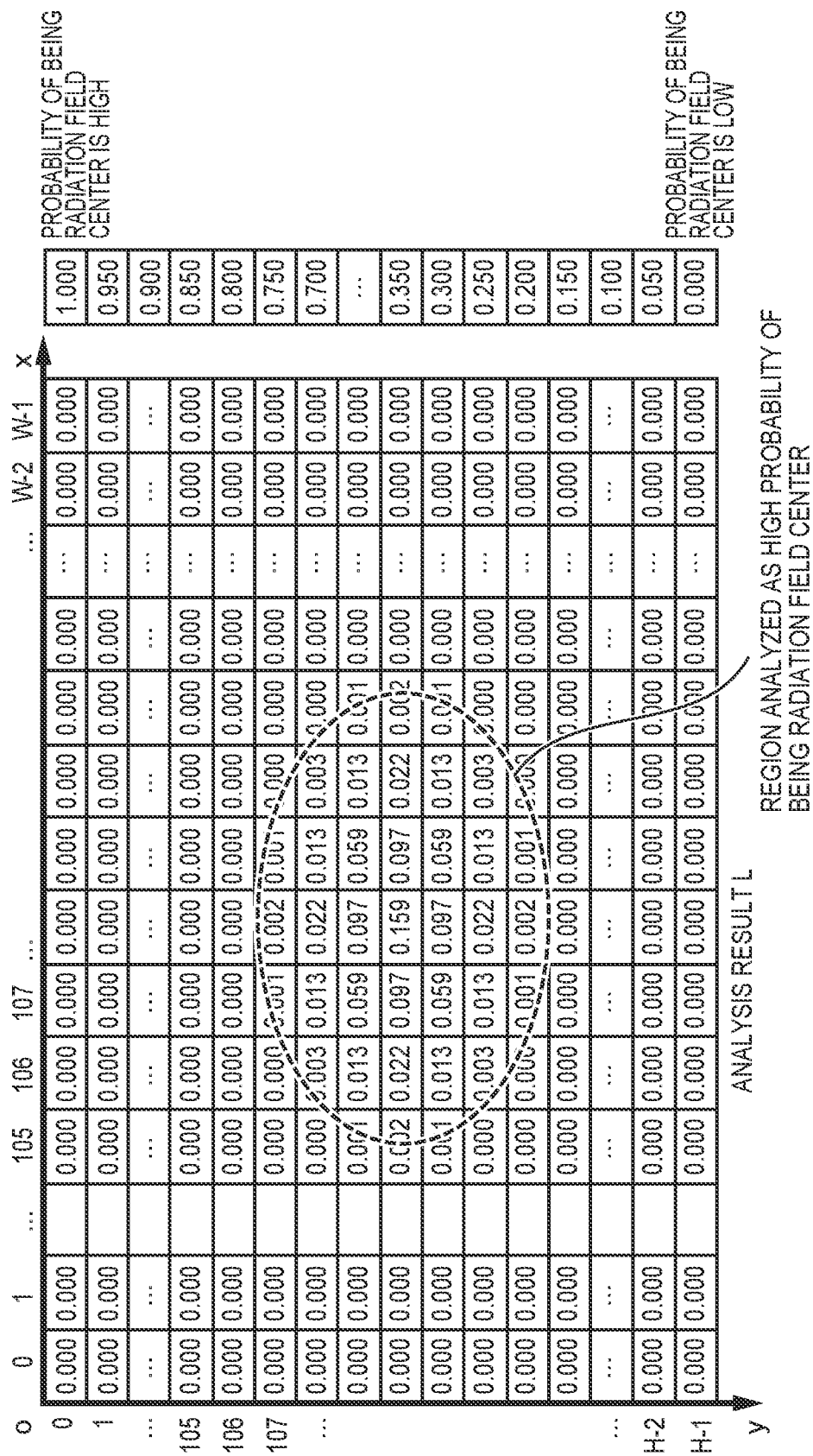
FIG. 5 is a view showing an example of an output of an image analysis unit 115.

The image analysis unit 115 analyzes the transferred radiation image (image data I) and generates an analysis result L of the radiation field. For example, the image analysis unit 115 analyzes the image data I, determines the degree that each position (for example, each pixel) of the radiation image becomes a predetermined portion of the radiation field, and generates the analysis result L representing the distribution of determined degrees. In this example, the predetermined portion of the radiation field is a radiation field center. Hence, the analysis result L is obtained as, for example, image data having, as a pixel value, a value representing that a pixel value is a radiation field center. However, the analysis result L is not limited to this. In this embodiment, for example, as shown in FIG. 5, the analysis result L is image data having the same size (W, H) as the image data I, and the probability that a value L(x, y) at the coordinates (x, y) is a radiation field center is represented by a value from 0 to 1. Concerning a method of generating the analysis result L, several detailed examples will be described below. However, the method of generating the analysis result L is not limited to the generation methods to be described below.

(Detailed Example 1 of Image Analysis)

As the first example of image analysis, a method of estimating a radiation field by threshold-processing image data and acquiring a radiation field center from the estimated radiation field will be described. In this method, for example, the image analysis unit 115 binarizes the image data I using a predetermined threshold T, thereby acquiring a binary image B.

$$B(x, y) = \begin{cases} 1 & I(x, y) \geq T \\ 0 & \text{otherwise} \end{cases} \quad (4)$$

Here, assume that the image data I is data that takes a large value if the incident dose to the radiation detector 105 is large. If image data is binarized, a high pixel value side, that is, the coordinates (x, y) for which B(x, y)=1 correspond to a radiation field. Note that the threshold T is a value statistically considered as appropriate and is stored in the storage unit 109 in advance as a parameter. However, the method is not limited to this, as a matter of course. The image analysis unit 115 may obtain the threshold T using an image analysis method such as discrimination analysis.

Next, the image analysis unit 115 obtains, from the region where B(x, y)=1, a gravity center $(x_g, y_g)$ by $$x_g = \frac{\sum_{y=0}^{H-1}\sum_{x=0}^{W-1} x \times B(x, y)}{\sum_{y=0}^{H-1}\sum_{x=0}^{W-1} B(x, y)}, y_g = \frac{\sum_{y=0}^{H-1}\sum_{x=0}^{W-1} y \times B(x, y)}{\sum_{y=0}^{H-1}\sum_{x=0}^{W-1} B(x, y)} \quad (5)$$

The gravity center obtained by equation (5) is used as the radiation field center $(x_g, y_g)$ by image analysis. The analysis result L according to this embodiment is obtained by converting the radiation field center $(x_g, y_g)$ by image analysis into a probability distribution by $$L(x, y) = \frac{1}{2\pi\sigma^2} \exp\left\{-\frac{(x-x_i)^2 + (y-y_i)^2}{2\sigma^2}\right\} \quad (6)$$

Note that the range in equation (6) is larger than 0. At the coordinates (x, y) that cannot be a radiation field center, or the coordinates (x, y) at which L(x, y) takes a sufficiently small value, L(x, y) is set to 0, thereby setting coordinates whose probability of being a radiation field is 0. In addition, $\sigma^2 \leq \pi/2$ is set such that the value L(x, y) becomes 1 or less. Here, $\sigma$ is a parameter for controlling the spread of a probability distribution representing the analysis result L. Preferably, $\sigma$ is set to a large value if the reliability of a radiation field center by image analysis is low, and set to a small value if the reliability is high. Hence, the maximum value of L(x, y) generally takes a value smaller than 1. In the above-described method using the threshold T, if the incident dose to the radiation detector 105 is large, the radiation field and the region outside the radiation field can easily be discriminated. Hence, the reliability is high. However, if the incident dose is small, the radiation field and the region outside the radiation field can hardly be discriminated. Hence, the reliability is low.

(Detailed Example 2 of Image Analysis)

The image analysis unit 115 extracts, from the image data I, the radiation field of radiation with which the radiation detector 105 is irradiated using processing such as edge detection or Hough transform, and obtains the center of the radiation field as the radiation field center $(x_g, y_g)$ by image analysis. When this method is used, the reliable radiation field center $(x_g, y_g)$ can be obtained although the calculation amount is larger than in the above-described binarization method using a threshold. In this case, a smaller value can be set to $\sigma$ when obtaining the analysis result L using equation (6).

(Detailed Example 3 of Image Analysis)

The image analysis unit 115 projects the image data I in the horizontal direction (x-axis direction) and the vertical direction (y-axis direction) to form projection data, and obtains the radiation field center $(x_g, y_g)$ by image analysis from the projection data. The projection data is obtained by averaging the pixel values of the image data I in the horizontal direction (x-axis direction) and the vertical direction (y-axis direction). This method is simpler than Detailed Examples 1 and 2 described above. Here, when projection data obtained by averaging the pixel values of the image data I in the x-axis direction is defined as Dx, and projection data obtained by averaging the pixel values in the y-axis direction is defined as Dy, the projection data Dx and Dy can be represented by $$Dx(y) = \frac{1}{W}\sum_{x=0}^{W-1} I(x, y), Dy(x) = \frac{1}{H}\sum_{y=0}^{H-1} I(x, y) \quad (7)$$

Figure 6:
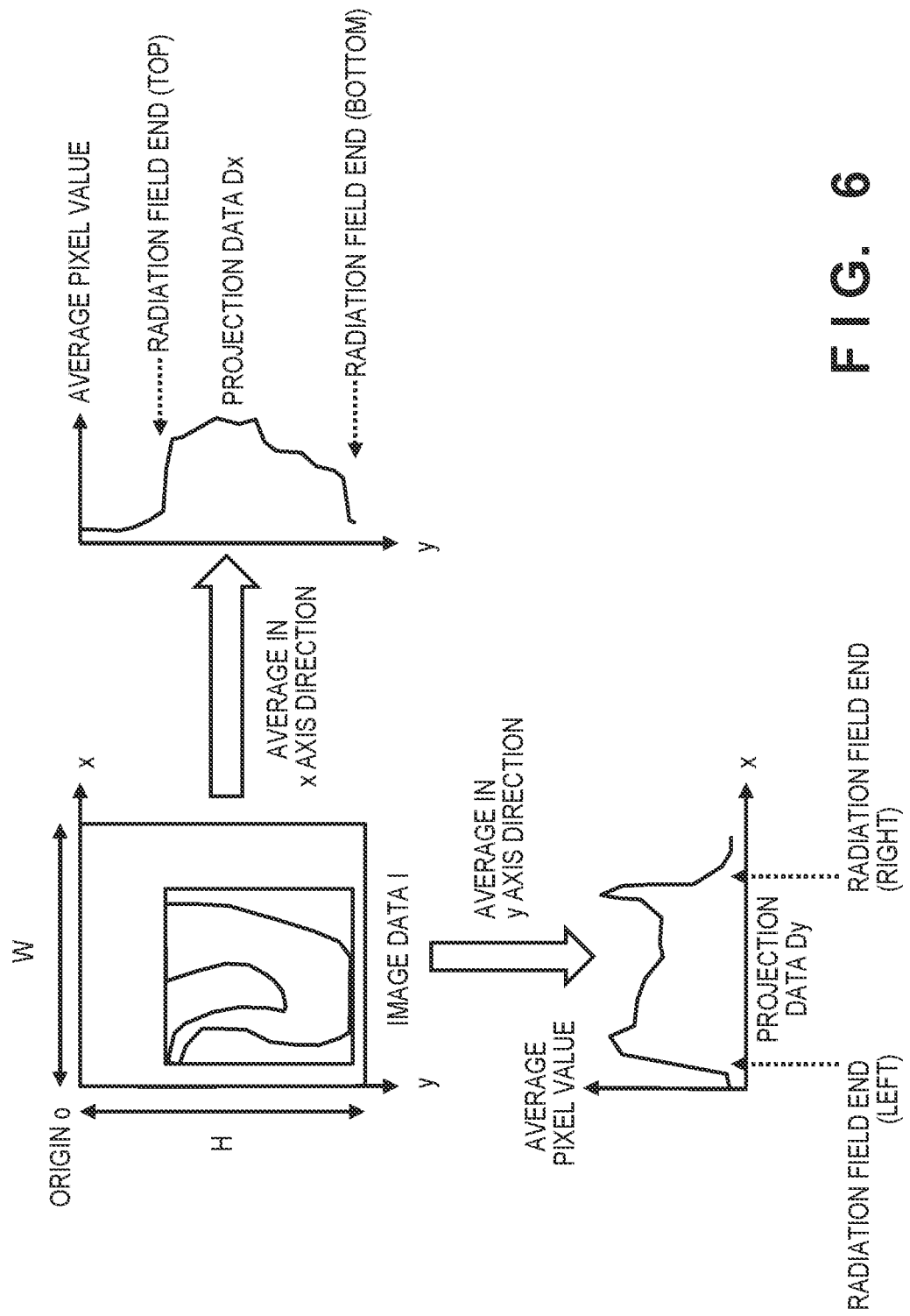
FIG. 6 is a view showing a detailed example of the image analysis unit 115.

FIG. 6 schematically shows the relationship between the projection data Dx and Dy and the image data I. As shown in FIG. 6, each of the projection data Dx and Dy is one-dimensional data having a distribution largely changing between the radiation field and the region outside the radiation field. Hence, when a position where the difference between adjacent data is large is extracted, a radiation field end can be acquired relatively easily. Upper, lower, left, and right ends $y_{top}$, $y_{bottom}$, $x_{left}$, and $x_{right}$ of a radiation field are acquired from the projection data Dx and Dy by, for example, $$y_{top} = \arg\max_y(Dx(y+1) - Dx(y-1))$$

$$y_{bottom} = \arg\min_y(Dx(y+1) - Dx(y-1))$$

$$x_{left} = \arg\max_x(Dy(x+1) - Dy(x-1))$$

$$x_{right} = \arg\max_x(Dy(x+1) - Dy(x-1)) \quad (8)$$

In equations (8), $\arg\max_y(\ )$ represents the value y when the value in the parentheses is maximized, and $\arg\min_y(\ )$ represents the value y when the value in the parentheses is minimized. Also, $\arg\max_x(\ )$ represents the value x when the value in the parentheses is maximized, and $\arg\min_x(\ )$ represents the value x when the value in the parentheses is minimized. From the thus obtained upper, lower, left, and right ends $y_{top}$, $y_{bottom}$, $x_{left}$, and $x_{right}$ of the radiation field, the radiation field center $(x_g, y_g)$ by image analysis can be obtained by, for example, equation (9). Then, when the radiation field center obtained by equation (9) is applied to equation (6) described above, the analysis result L can be obtained.

$$x_g = \frac{x_{left} + x_{right}}{2}, y_g = \frac{y_{top} + y_{bottom}}{2} \quad (9)$$

(Detailed Example 4 of Image Analysis)

The image analysis unit 115 may be configured to generate an inference device that infers a radiation field center by machine learning and obtain the radiation field center ($x_g$, $y_g$) by image analysis using the inference device. The inference device can be generated in advance by supervised learning (preferably, deep learning of a model constructed by including a neural network) using, as supervised data, a combination of a number of radiation images and correct answer positions of radiation field centers corresponding to the radiation images. The inference device is a calculation model that, when image data is input, calculates an inference result of a radiation field center using a number of parameters generated by learning. The radiation field center ($x_g$, $y_g$) generated by the inference device is converted into the analysis result L using equation (6). Since the output of the inference device generated by machine learning using a number of supervised data is reliable in general, the value σ in equation (6) can be set small.

Note that in the method by machine learning, an inference device that directly outputs the analysis result L may be generated in place of the inference device that outputs the radiation field center ($x_g$, $y_g$). The inference device that outputs the analysis result can be generated by supervised learning (preferably, deep learning of a model constructed by including a neural network) using, as supervised data, a combination of a number of radiation images and probability distributions converted using equation (6) from radiation field centers corresponding to the radiation images. The thus configured inference device outputs the analysis result L when the image data I is given. Hence, the analysis result output from the inference device can directly be used as the output of the image analysis unit 115.

As described above, the method of generating the analysis result L of the radiation field by the image analysis unit 115 is not particularly limited, and an appropriate method is used in accordance with usable information, required accuracy and processing speed, and the like.

[Step S203]

The radiation field recognition unit 113 transfers the prediction result P output from the prediction unit 114 and the analysis result L output from the image analysis unit 115 to the combining unit 116 via the CPU bus 119. The combining unit 116, for example, combines the prediction result P and the analysis result L by equation (10), thereby calculating a combining result C. In equation (10), for corresponding positions of the prediction result P and the analysis result L, values (degrees that a position is a radiation field center) are multiplied, thereby obtaining the combining result C. However, the combining method is not limited to this, and, for example, P(x, y) and L(x, y) in equation (10) may be weighted and multiplied to combine.

$$C(x,y)=P(x,y)L(x,y) \quad (10)$$

As described above, in this embodiment, the prediction result P and the analysis result L are image data having the same size as the image data I, and each of the values P(x, y) and L(x, y) at the coordinates (x, y) represents the probability that the value is a radiation field center by a value from 0 to 1. Hence, the combining result C that is the product of these values is image data having the same size as the image data I, and a value C(x, y) at the coordinates (x, y) represents the probability that the value is a radiation field center by a value from 0 to 1.

[Step S204]

The radiation field recognition unit 113 transfers the combining result C output from the combining unit 116 to the recognition unit 117 via the CPU bus 119. The recognition unit 117 decides the radiation field center ($x_c$, $y_c$) from the combining result C by $$(x_c, y_c) = \arg\max_{x,y}(C(x,y)) \quad (11)$$

In equation (11), $\arg\max_{x,y}(\ )$ represents the value of (x, y) when the value in the parentheses is maximized. The obtained radiation field center ($x_c$, $y_c$) is output from the radiation field recognition unit 113 as radiation field information. Note that if a plurality of radiation field centers are acquired by equation (11), for example, the gravity center position of these is decided as the radiation field center. Alternatively, a predetermined number of coordinates may be acquired in descending order of $\arg\max_{x,y}(\ )$, and the gravity center position of these may be decided as the radiation field center.

A method of obtaining the radiation field center ($x_c$, $y_c$) as radiation field information acquired by radiation field recognition has been described above. As described above, the image processing unit 118 performs, for example, statistic amount acquisition, mask processing, image cut-out, and the like using the radiation field information output from the radiation field recognition unit 113. Hence, the radiation field information is preferably information representing not a point but a region. For example, in this embodiment, using the fact that the radiation field has a rectangular shape in the fixed size ($W_c$, $H_c$), the radiation field recognition unit 113 converts the radiation field center coordinates into the region of the radiation field by equations (12). In equation (12), the radiation field center coordinates are converted into coordinates ($x_{left}$, $y_{top}$) of the upper left end and coordinates ($x_{right}$, $y_{bottom}$) of the lower right end of the radiation field, thereby acquiring the rectangular region of the radiation field.

$$\begin{aligned} x_{left} &= x_c - \frac{W_c}{2} \\ y_{top} &= y_c - \frac{H_c}{2} \\ x_{right} &= x_{left} + W_c \\ y_{bottom} &= y_{top} + H_c \end{aligned} \quad (12)$$

A case in which the center coordinates ($x_c$, $y_c$) of the radiation field having a rectangular shape in the fixed size ($W_c$, $H_c$) are used as the radiation field information has been described above. However, the present invention is not limited to this. As the radiation field information, a predetermined portion capable of specifying a radiation field end can be used. As the predetermined portion, for example, the position of a vertex of a polygon representing the radiation field, a side that forms a polygon representing the radiation field, or the like can be used in addition to the position of the center of the radiation field. For example, more generally, considering a case in which the radiation field has a polygonal shape other than a rectangular shape, the method can be applied to a case in which N vertices of a polygon are used as the radiation field information. In this case, for each of the N vertices, the prediction unit 114 generates the prediction result P, the image analysis unit 115 generates the analysis result L, and the combining unit 116 generates the combining result C. The recognition unit 117 recognizes, as a radiation field region, a polygon obtained by connecting N vertices obtained from N combining results C by lines. In this case, for each vertex, the prediction unit 114 generates the prediction result P of each vertex using coordinate positions acquired from prior information, and the image analysis unit 115 analyzes the image data I to obtain the analysis result L for each vertex. The combining unit 116 combines the prediction result P and the analysis result L for each vertex, thereby obtaining the combining result C for each vertex.

Also, this method can be applied even if the radiation field information represents not the coordinates of a center point or a vertex but image information representing a line (a side of a polygon). For example, the prediction result P of the prediction unit 114, the analysis result L of the image analysis unit 115, and the combining result C of the combining unit 116 are generated for points on projection data generated by projecting an image onto the x-axis and the y-axis. For example, each of the prediction result P and the analysis result L is generated to represent the probability distribution of an end position (edge position) of a radiation field on the projection data. When peaks of the combining result C are acquired on the projection data by applying the above-described method, the peaks represent lines that are parallel to the x-axis and the y-axis and surround the radiation field, and can be used as radiation field information. Note that described above is the simplest example in a case in which lines are used. To cope with a more complex shape, a radiation image may be Hough-transformed, and the prediction result P, the analysis result L, and the combining result C may be calculated on a Hough plane. In this case, lines represented by peaks acquired from the combining result C on the Hough plane indicate lines surrounding a polygonal radiation field and can be used as radiation field information.

Also, the radiation field information may be not the coordinates of a center point or a vertex or image information representing a line but image information representing a region. In this case, each of the prediction result P of the prediction unit 114, the analysis result L of the image analysis unit 115, and the combining result C of the combining unit 116 is generated as a probability map representing, for each pixel, the probability that the pixel is a radiation field center by a value from 0 to 1. Using the predetermined threshold T (for example, T=0.5), it is determined, for each pixel of the combining result C, whether the pixel belongs to a radiation field, thereby acquiring radiation field information as, for example, a binary image. A morphological operation such as expansion/contraction processing is performed for the obtained binary image, or regions other than a connecting regions of the largest area are excluded by labeling, thereby obtaining desired radiation field information.

As described above, according to the first embodiment, a radiation field is recognized using prediction of a radiation field based on image data and the analysis result of the radiation field from an image, thereby enabling radiation field recognition with real time property and stability.

Second Embodiment

In the first embodiment, a configuration for recognizing a radiation field from the image data I has been described. The configuration for recognizing a radiation field from the image data I can be used for both independent radiation imaging and fluoroscopic imaging. In the second embodiment, a configuration capable of performing more stable radiation field detection particularly in fluoroscopic imaging by referring to an irradiation recognition result for a past frame will be described. Note that the configuration of a radiation imaging apparatus according to the second embodiment is the same as in the first embodiment (FIG. 1). A fluoroscopy instruction input from a user via an operation unit 111 is transmitted to a data collection unit 106 by a CPU 108. Upon receiving the fluoroscopic instruction, the data collection unit 106 controls a radiation generation unit 101 and a radiation detector 105 to cause these to execute radioscopy.

In the radioscopy, during reception of the fluoroscopy instruction, the radiation generation unit 101 irradiates an object 104 with a radiation beam 103 continuously or as pulsatively. The radiation beam 103 emitted by the radiation generation unit 101, whose irradiation range is limited by a radiation diaphragm 102, passes through the object 104 and reaches the radiation detector 105. The radiation detector 105 outputs a signal according to the intensity of the radiation beam 103 that has reached.

The data collection unit 106 converts the signal output from the radiation detector 105 into a digital signal at a predetermined interval, and supplies it as time-series image data to a preprocessing unit 107. The preprocessing unit 107 performs preprocessing such as offset correction and gain correction for each frame that forms the time-series image data supplied from the data collection unit 106. The time-series image data that has undergone the preprocessing by the preprocessing unit 107 is sequentially transferred to a main memory 110, a radiation field recognition unit 113, and an image processing unit 118 via a CPU bus 119.

The radiation field recognition unit 113 recognizes, from the transferred time-series image data, a radiation field where the radiation detector 105 is irradiated with the radiation, and outputs radiation field information representing the radiation field. That is, the radiation field recognition unit 113 recognizes the radiation field of a time-serially acquired radioscopic image. The recognized radiation field is a predetermined portion capable of specifying a radiation field end, and the predetermined portion is, for example, the position of the center of the radiation field, the position of a vertex of a polygon representing the radiation field, or a side that forms a polygon representing the radiation field. The radiation field recognition unit 113 predicts the predetermined portion of the radiation field of the target fluoroscopic image (for example, the current frame) that is the radioscopic image of the decision target based on prior information acquired before the target fluoroscopic image. As the prior information, control information of the radiation diaphragm for setting the radiation field region of the target fluoroscopic image (current frame), and radiation field information representing the radiation field region of a preceding fluoroscopic image (for example, a preceding frame) acquired before the target fluoroscopic image can be used.

The control information (called diaphragm control information) of the radiation diaphragm is information for controlling the radiation diaphragm 102. By receiving the diaphragm control information, the radiation diaphragm 102 moves and changes the position or size of a rectangular opening formed by the radiation diaphragm 102. When the opening is changed by the radiation diaphragm 102, the radiation field of the radiation with which the radiation detector 105 is irradiated changes, and a target fluoroscopic image is obtained. That is, a time lag occurs from the reception of the diaphragm control information by the radiation diaphragm 102 to the obtaining of the target fluoroscopic image.

Also, the radiation field information of a preceding fluoroscopic image is a recognition result of a radiation field region specified in a past fluoroscopic image acquired before the target fluoroscopic image, and corresponds to a combining result Cm to be described later. Note that the radiation field information of the preceding fluoroscopic image may include information representing a predetermined portion capable of specifying a radiation field end of the preceding fluoroscopic image and diaphragm control information that sets the preceding fluoroscopic image. Also, the radiation field information of the preceding fluoroscopic image is not limited to the radiation field information of a frame immediately before the target fluoroscopic image. The frame may be a frame one or more cycles before, and radiation field information corresponding to two or more frames may be used.

In this way, the radiation field recognition unit 113 predicts the predetermined portion of the radiation field in the target fluoroscopic image based on the prior information (the diaphragm control information and the radiation field information of the preceding fluoroscopic image) acquired before the target fluoroscopic image. Note that the radiation field recognition unit 113 may predict the predetermined portion of the radiation field in the target fluoroscopic image from one of the diaphragm control information and the radiation field information of the preceding fluoroscopic image.

In addition, the radiation field recognition unit 113 analyzes the predetermined portion of the radiation field in the target fluoroscopic image. The radiation field recognition unit 113 decides the radiation field region of the target fluoroscopic image based on prediction information representing a prediction result and image information representing an analysis result. The radiation field recognition unit 113 outputs radiation field information representing the decided radiation field region. The image processing unit 118 performs image processing based on the radiation field information output from the radiation field recognition unit 113 for the transferred time-series image data. The image processing can include, for example, tone processing based on the statistic values of pixel values belonging to the radiation field, such as the average value and the maximum/minimum value, cut-out/enlargement processing of only pixels belonging to the radiation field, and mask processing of pixels that do not belong to the radiation field. The time-series radiation field information and the time-series image data that has undergone the image processing by the image processing unit 118 are transferred to, for example, a storage unit 109 and a display unit 112 via the CPU bus 119 as time-series image data that has undergone image processing.

The storage unit 109 stores the transferred time-series radiation field information and the time-series image data that has undergone image processing. The display unit 112 displays the transferred time-series radiation field information and the time-series image data that has undergone image processing. Since the time-series image data is displayed while being switched at the same interval as the image data acquisition in fluoroscopy, the user visually recognizes the time-series image as a moving image. The user confirms the time-series radiation field information and the time-series image data that has undergone image processing, which are displayed, and inputs an operation instruction via the operation unit 111 as needed.

In the above-described radioscopy, the radiation field recognition unit 113 recognizes a radiation field from each frame of the time-series image data and outputs radiation field information. This operation of the radiation field recognition unit 113 will be described below in detail with reference to a flowchart shown in FIG. 7. Note that each image data (frame) that forms time-series image data to be input is represented by In using n that represents a frame number from the start of fluoroscopy. In the second embodiment as well, a configuration for obtaining center coordi-nates $(x_c, y_c)$ of a rectangular radiation field with a fixed size $(W_c, H_c)$ as radiation field information will be described. That is, a configuration for sequentially recognizing radiation field center coordinates $(x_c n, y_c n)$ from the image data In of the frame number n acquired in fluoroscopic imaging will be described (FIG. 8).

(Radiation Field Recognition Procedure)

[Step S701]

At the start of fluoroscopy, that is, when frame number n=1, in the radiation field recognition unit 113, a prediction unit 114 predicts the radiation field of image data I1 and generates a prediction result P1 for frame number n=1. The method of obtaining the prediction result P1 is the same as the method of obtaining the prediction result P described concerning step S201. For frame number n=1, steps S702 to S704 to be described below are executed.

[Step S702]

In the radiation field recognition unit 113, an image analysis unit 115 analyzes the transferred input image data In of the frame number n, and generates an analysis result Ln of the radiation field for the frame number n. The method of obtaining the analysis result Ln is the same as the method of obtaining the analysis result L described concerning step S202.

[Step S703]

The radiation field recognition unit 113 transfers a prediction result Pn output from the prediction unit 114 and the analysis result Ln output from the image analysis unit 115 for the frame number n to a combining unit 116 via the CPU bus 119. The combining unit 116 calculates a combining result Cn based on the prediction result Pn and the analysis result Ln. The method of obtaining the combining result Cn is the same as the method of obtaining the combining result C described concerning step S203. The combining result Cn is transmitted to the storage unit 109 via the CPU bus 119 and stored.

[Step S704]

The radiation field recognition unit 113 transfers the combining result Cn output from the combining unit 116 for the frame number n to a recognition unit 117 via the CPU bus 119. The recognition unit 117 obtains the radiation field center $(x_c n, y_c n)$ for the frame number n from the combining result Cn. The method of obtaining the radiation field center $(x_c n, y_c n)$ is the same as the method of obtaining the radiation field center $(x_c, y_c)$ described concerning step S204, and a detailed description thereof will be omitted. The thus obtained radiation field center $(x_c n, y_c n)$ is output from the radiation field recognition unit 113 as radiation field information for the frame number n.

[Step S705]

The radiation field recognition unit 113 determines whether a fluoroscopy instruction from the user via the operation unit 111 indicates continuation of fluoroscopy. If the fluoroscopy instruction from the user via the operation unit 111 is ended (NO in step S705), the processing is ended. If the fluoroscopy instruction from the user via the operation unit 111 continues for frame number n>1 as well (YES in step S705), the process advances to step S706.

[Step S706]

The prediction unit 114 predicts the radiation field of the input image data In and generates the prediction result Pn. In step S706, however, prediction processing different from the prediction processing in step S701 (prediction processing for n=1) is applied. If the frame number n of radioscopy>1, the prediction unit 114, for example, calculates the prediction result Pn of the nth frame based on the combining result Cm of the mth frame (m<n) in the past, as indicated by equation (13) below. The combining result Cm corresponds to the above-described radiation field information of a preceding fluoroscopic image. That is, the prediction unit 114 reads out the combining result Cm of the past frame from the storage unit 109 as the prediction result Pn. For example, if the combining result of the immediately preceding frame is used, m=n−1.

$$Pn(x,y)=Cm(x,y) \quad (13)$$

The prediction result Pn may be adjusted by adding other prior information to the combining result Cm of the past frame. As an example of such adjustment, adjustment using control information representing a moving direction (vx, vy) when the user moves the radiation diaphragm 102 via the operation unit 111 will be described here. The control information representing the moving direction corresponds to the above-described diaphragm control information and input as prior information to the prediction unit 114 via the CPU bus 119. The prediction unit 114 adjusts the combining result Cm of the radiation field based on the moving direction (vx, vy) serving as prior information, as indicated by equation (14). Note that in equation (14), k is a coefficient considering the movable speed of the radiation diaphragm or the like. According to this adjustment, since the current prior information can be added to the combining result Cm of the past frame, more stable prediction can be performed. After that, the process returns to step S702, and the radiation field recognition unit 113 repeats the above-described operation. Note that in equation (14), if x−k×vx does not fall within the range of 0 to W, or if y−k×vy does not fall within the range of 0 to H, Pn(x, y)=0 is set.

$$Pn(x,y)=Cm(x-k \times vx, y-k \times vy) \quad (14)$$

As described above, according to the second embodiment, when the combining result Cm of the past frame is used, time-serially accumulated past information is used as prior information, and stable radiation field recognition in radioscopy can be performed. Also, when the moving direction of the radiation diaphragm 102 or the like is added as prior information, the stability of radiation field recognition in radioscopy can be further improved.

Note that in the above description, an example in which when the prediction unit 114 acquires the prediction result P in step S706, the combining result Cm generated in the past frame is used as prior information has been described. However, the present invention is not limited to this. For example, a prediction result Pm and an analysis result Lm generated in the past frame may be used as prior information in step S706. Also, in step S704, the recognition unit 117 may adjust the radiation field center $(x_c n, y_c n)$ that is a combining result using a radiation field center $(x_c m, y_c m)$ that is radiation field information generated in the past frame. For example, in step S704, the radiation field center $(x_c n, y_c n)$ obtained from the current frame may be updated by equations (15) using the radiation field center $(x_c m, y_c m)$ of the past frame and a predetermined coefficient α. This smooths such that variations of the predetermined portion (for example, the position of a radiation center) of the radiation field decided for a plurality of time-serially acquired radiation images (frames) temporally continue. Hence, this can suppress a vibration of radiation field information for each frame and increase the stability in radiation field detection.

$$x_c n \leftarrow \alpha \times x_c n + (1-\alpha) \times x_c m$$

$$y_c n \leftarrow \alpha \times y_c n + (1-\alpha) \times y_c m \quad (15)$$

As described above, according to the first and second embodiments, since a radiation field is recognized using prediction of a radiation field based on prior information and a result of analyzing a radiation field from an image, stable radiation field recognition is implemented. Particularly in radioscopy, when a radiation field recognition result concerning a frame acquired in the past is used as prior information, radiation field recognition with real time property and stability can be performed.

Also, in the above-described embodiments, an example in which the radiation field region of a radiation image is obtained based on a prediction result predicted based on prior information and the analysis result of the radiation image has been described. However, the present invention is not limited to this. For example, the radiation field region of a radiation image may be obtained using a prediction result predicted based on prior information for analysis of the radiation image. For example, the radiation field recognition unit 113 may predict a predetermined portion of a radiation field in a target fluoroscopic image (for example, a current frame) based on prior information (diaphragm control information and radiation field information of a preceding fluoroscopic image), and narrows down the range to analyze the target fluoroscopic image based on the prediction result. This can shorten the time to analyze the target fluoroscopic image. In addition, the radiation field recognition unit 113 may specify the radiation field region based on a predetermined portion of the radiation field specified in the narrowed range.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-109951, filed Jun. 25, 2020, which is hereby incorporated by reference herein in its entirety.

What is claimed is:

1. An image processing apparatus for determining a radiation field of radiation from a radiation image, comprising:
    a processor; and
    a memory, including instructions thereon, which when executed by the processor cause the apparatus to:
    predict, based on information related to the radiation image and prior information, a degree that each position of the radiation image becomes a predetermined portion of the radiation field and generate a prediction result representing a distribution of the predicted degrees;
    analyze the radiation image to determines the degree that each position of the radiation image becomes the predetermined portion of the radiation field and generate an analysis result representing the distribution of the predicted degrees; and
    decide the predetermined portion of the radiation field based on a combining result obtained by combining the prediction result and the analysis result.

2. The apparatus according to claim 1, wherein the predetermined portion of the radiation field is a position of a center of the radiation field.

3. The apparatus according to claim 1, wherein the predetermined portion of the radiation field is a position of a vertex of a polygon representing the radiation field.

4. The apparatus according to claim 1, wherein the predetermined portion of the radiation field is a side that forms a polygon representing the radiation field.

5. The apparatus according to claim 1, wherein the predetermined portion of the radiation field is a position of a pixel of the radiation image, which belongs to the radiation field.

6. The apparatus according to claim 1, wherein the instructions, when executed by the processor, further cause the apparatus to:
    predict a position of the predetermined portion of the radiation field based on the prior information, and
    generate the prediction result using a distribution function and the predicted position of the predetermined portion.

7. The apparatus according to claim 6, wherein
    the prior information represents a plurality of positions for the predetermined portion, and
    wherein the instructions, when executed by the processor, further cause the apparatus to: generate the prediction result by combining distributions of degrees predicted for the plurality of positions.

8. The apparatus according to claim 6, wherein the prior information designates the distribution function.

9. The apparatus according to claim 6, wherein
    the prior information includes, as information concerning an object that is a target of radiation imaging, one of a physical size and an imaging part of the object, and
    wherein the instructions, when executed by the processor, further cause the apparatus to: predict the position of the predetermined portion based on the information concerning the object.

10. The apparatus according to claim 6, wherein
    the prior information includes a designation of the predetermined portion in the radiation image, which is input by a user, and
    wherein the instructions, when executed by the processor, further cause the apparatus to: use a position designated by the user as the position of the predetermined portion.

11. The apparatus according to claim 1, wherein the instructions, when executed by the processor, further cause the apparatus to:
    determine the position of the predetermined portion of the radiation field by analyzing the radiation image, and
    generates the analysis result using the determined position of the predetermined portion and the distribution function.

12. The apparatus according to claim 11, wherein the instructions, when executed by the processor, further cause the apparatus to: determine the position of the predetermined portion based on a radiation field extracted from the radiation image by image analysis using at least one of threshold processing, edge detection, and Hough conversion.

13. The apparatus according to claim 11, wherein the instructions, when executed by the processor, further cause the apparatus to: determine the position of the predetermined portion of the radiation field from the radiation image using an inference device generated by machine learning using supervised data including a radiation image and a correct answer position of the predetermined portion of the radiation field.

14. The apparatus according to claim 1, wherein the instructions, when executed by the processor, further cause the apparatus to: obtain the combining result by multiplying the degrees for corresponding positions of the prediction result and the analysis result.

15. The apparatus according to claim 1, wherein the instructions, when executed by the processor, further cause the apparatus to: generate the prediction result for an nth radiation image of a plurality of time-serially acquired radiation images based on at least one of the prediction result, the analysis result, and the combining result generated for an mth (n>m) radiation image.

16. The apparatus according to claim 1, wherein the information related to the radiation image is size information of the radiation image.

17. An image processing method of determining a radiation field of radiation from a radiation image, comprising:
    predicting, based on information related to the radiation image and prior information, a degree that each position of the radiation image becomes a predetermined portion of the radiation field and generating a prediction result representing a distribution of the predicted degree;
    analyzing the radiation image to determines the degree that each position of the radiation image becomes the predetermined portion of the radiation field and generating an analysis result representing the distribution of the predicted degree; and
    deciding the predetermined portion of the radiation field based on a combining result obtained by combining the prediction result and the analysis result.

18. A non-transitory computer-readable storage medium storing a program for causing a computer to execute an image processing method of determining a radiation field of radiation from a radiation image, the method comprising:
    predicting, based on information related to the radiation image and prior information, a degree that each position of the radiation image becomes a predetermined portion of the radiation field and generating a prediction result representing a distribution of the predicted degree;

analyzing the radiation image to determines the degree that each position of the radiation image becomes the predetermined portion of the radiation field and generating an analysis result representing the distribution of the predicted degree; and deciding the predetermined portion of the radiation field based on a combining result obtained by combining the prediction result and the analysis result.

19. An image processing apparatus for deciding a radiation field region of a time-serially acquired radioscopic image, comprising:

processor; and a memory, including instructions thereon, which when executed by the processor cause the apparatus to:

predict a predetermined portion of a radiation field in a target fluoroscopic image that is a radioscopic image of a decision target based on information related to the radioscopic image and prior information acquired before the target fluoroscopic image and acquiring prediction information representing a prediction result of the prediction;

analyze the target fluoroscopic image and acquiring image information representing the predetermined portion of the radiation field in the target fluoroscopic image; and decide the radiation field region of the target fluoroscopic image based on the prediction information and the image information.

20. The apparatus according to claim 19, wherein the instructions, when executed by the processor, further cause the apparatus to: acquire, as the prior information, at least one of control information of a radiation diaphragm configured to set the radiation field region of the target fluoroscopic image and radiation field information representing a radiation field region of a preceding fluoroscopic image that is a radioscopic image acquired before the target fluoroscopic image, and predicts the predetermined portion of the radiation field in the target fluoroscopic image based on the acquired prior information.

* * * * *